United States Patent [19]
Eldin

[11] Patent Number: 5,919,944
[45] Date of Patent: Jul. 6, 1999

[54] POLYMERISABLE DIKETOPYRROLOPYRROLES

[75] Inventor: Sameer Eldin, Courtepin, Switzerland

[73] Assignee: Ciba Specialty Chemicals Corporation, Tarrytown, N.Y.

[21] Appl. No.: 09/119,434

[22] Filed: Jul. 20, 1998

[30] Foreign Application Priority Data

Jul. 30, 1997 [CH] Switzerland ............... 1822/97

[51] Int. Cl.$^6$ ............ C07D 487/02; C07D 209/40; C07D 213/06; C07D 401/04
[52] U.S. Cl. ............ 548/453; 548/512; 548/186; 548/240; 548/243; 548/314.7; 548/316.7; 548/406; 548/412; 546/348; 546/270.4; 546/269.7; 546/183; 546/14; 546/24; 544/14; 544/24; 544/361; 544/255; 534/560; 534/561; 8/552
[58] Field of Search ............ 548/453, 512, 548/186, 240, 243, 314.7, 316.7, 406, 412; 546/348, 270.4, 269.7, 183, 14, 24; 544/361, 255, 129, 111, 14, 24; 534/560, 561; 8/552

[56] References Cited

U.S. PATENT DOCUMENTS

| | | | |
|---|---|---|---|
| 4,585,878 | 4/1986 | Jost et al. | 548/453 |
| 4,931,439 | 6/1990 | Kristinsson | 548/132 |
| 4,996,325 | 2/1991 | Kristinsson | 514/242 |
| 5,179,094 | 1/1993 | Kristiansen et al. | 514/242 |
| 5,354,869 | 10/1994 | Langhals et al. | 548/453 |
| 5,750,723 | 5/1998 | Eldin et al. | 548/453 |

FOREIGN PATENT DOCUMENTS

| | | |
|---|---|---|
| 0337951 | 10/1989 | European Pat. Off. |
| 0787731 | 8/1997 | European Pat. Off. |

OTHER PUBLICATIONS

Derwent Abstracts 97–387439 (36) (EP787731–A) (Aug. 13, 1997).
Chan, W–K et al., J. Amer. Chem. Soc, vol. 115(25), pp. 11735–11743 (1993).
Derwent Abstr. 89–302657/42 for EP 0337951.

*Primary Examiner*—Johann Richter
*Assistant Examiner*—Dominic Keating
*Attorney, Agent, or Firm*—Kevin T. Mansfield; Jacob M. Levine

[57] ABSTRACT

Diketopyrrolopyrroles of formula I

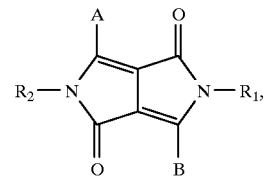

(I)

wherein $R_1$ is a radical of formula II

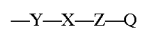

(II)

wherein

Y is $-CR_3R_4-$, $-SO_2-$, $-CO-$, $-Si(Hal)_2-$, $-POHal-$, wherein $R_3$ and $R_4$ are each independently of the other hydrogen or $C_1-C_4$alkyl, and Hal is halogen, X is an unsubstituted or substituted carbocylic or heterocyclic arylene group, Z is a single bond, uninterrupted linear or branched $C_1-C_{30}$alkylene, or linear or branched $C_2-C_{30}$alkylene which is interrupted once or more than once by a hetero atom, $-CH=CH-$, $-C\equiv C-$, $-N=CH-$, $-CH=N-$ or $-NH-$, or is $C_5-C_{12}$cycloalkylene, Q is a polyreactive functional group, and $R_2$ is $C_1-C_6$alkyl,

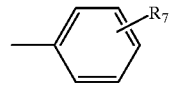

or $R_1$, and $R_7$ is hydrogen or $C_1-C_6$alkyl, and A and B are each independently of the other an unsaturated ring compound, as well as a process for the preparation of the diketopyrrolopyrroles I, their use for the preparation of polymers, polymers based on diketopyrrolopyrroles I, a process for their preparation, their method of using it, coloured high molecular weight organic materials comprising the inventive polymers, a monomer mixture comprising the inventive diketopyrrolopyrroles I as well as the method of using this monomer mixture.

3 Claims, No Drawings

POLYMERISABLE DIKETOPYRROLOPYRROLES

The present invention relates to diketopyrrolopyrroles of formula I

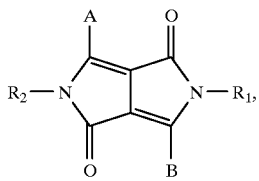
(I)

wherein $R_1$ is a radical of formula II

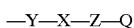
—Y—X—Z—Q (II), wherein

Y is —$CR_3R_4$—, —$SO_2$—, —CO—, —Si(Hal)$_2$—, —POHal—, wherein $R_3$ and $R_4$ are each independently of the other hydrogen or $C_1$–$C_4$alkyl, and Hal is halogen, X is an unsubstituted or substituted carbocyclic or heterocyclic arylene group, Z is a single bond, uninterrupted linear or branched $C_1$–$C_{30}$alkylene, or linear or branched $C_2$–$C_{30}$alkylene which is interrupted once or more than once by a hetero atom, —CH=CH—, —C≡C—, —N=CH—, —CH=N— or —NH—, or is $C_5$–$Cl_{12}$cycloalkylene, Q is —OH, —SH, —$NH_2$, glycidyl, 1,2-epoxyethyl,

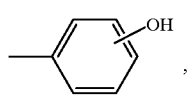,

—CHO, —NCO, —CH=$CH_2$, —C($CH_3$)=$CH_2$, —OCO—CH=$CH_2$, —OCO—C(Me)=$CH_2$, —$CH_2$-CH=$CH_2$, —$CH_2$—OH, —CO—CH=$CH_2$, —CO—C($CH_3$)=$CH_2$, $C_5$–$C_7$cycloalkenyl,

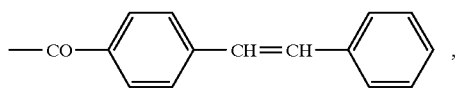,

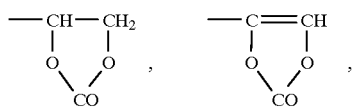,

—$CONHR_6$, —$COOR_6$, —$COR_6$, wherein $R_6$ is hydrogen or $C_1$–$C_6$alkyl,

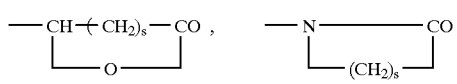

wherein s is an integer from 1 to 6, and $R_2$ is $C_1$–$C_6$alkyl,

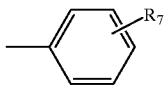

or $R_1$, and $R_7$ is hydrogen or $C_1$–$C_6$alkyl,
and

A and B are each independently of the other a group of formula

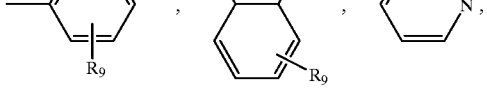

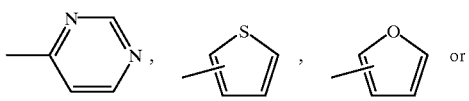

wherein $R_8$ and $R_9$ are each independently of the other hydrogen, halogen, $C_1$–$C_{18}$alkyl, $C_1$–$C_8$alkoxy, $C_1$–$C_{18}$alkylmercapto, $C_1$–$C_{18}$alkylamino, $C_1$–$C_{18}$alkoxycarbonyl, $C_1$–$C_{18}$alkylaminocarbonyl, —CN, —$NO_2$, trifluoromethyl, $C_5$–$C_6$cycloalkyl, —CH=N—($C_1$–$C_{18}$alkyl),

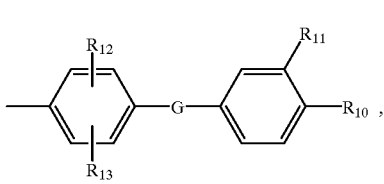

imidazolyl, pyrrazolyl, triazolyl, piperazinyl, pyrrolyl, oxazolyl, benzoxazolyl, benzothiazolyl, benzimidazolyl, morpholinyl, piperidinyl or pyrrolidinyl, G is —$CH_2$—, —CH($CH_3$)—, —C($CH_3$)$_2$—, —CH=N—, —N=N—, —O—, —S—, —SO—, —$SO_2$—, CONH— or —$NR_7$—, $R_{10}$ and $R_{11}$ are each independently of the other hydrogen, halogen, $C_1$–$C_6$alkyl, $C_1$–$C_{18}$alkoxy or —CN, $R_{12}$ and $R_{13}$ are each independently of the other hydrogen, halogen or $C_1$–$C_6$alkyl.

This invention also relates to a process for the preparation of the diketopyrrolopyrroles I, to their use for the preparation of polymers, to polymers based on diketopyrrolopyrroles I, to a process for their preparation, to their use, to coloured high molecular weight organic materials comprising the inventive polymers, to a monomer mixture comprising the inventive diketopyrrolopyrroles I as well as to the use of this monomer mixture.

EP-A 337 951 describes coloured polymer microparticles which may be obtained by copolymerising pigment derivatives containing polymerisable reactive groups and ethylenically mono- or polyunsaturated compounds and/or one or several glycidyl compounds and/or one or several different monomers selected from the group consisting of the polyalcohols, polycarboxylic acids, hydroxycarboxylic acids, lactones and aminocarboxylic acids. The numerous pigments possible as starting materials also include the diketopyrrolopyrrole ("DPP") derivatives which, at the each of the two nitrogen atoms, may carry one polymerisable group bound to an alkylene group. The polymeric compounds cited in EP-A 337 951 have the disadvantage of not being sufficiently photostable.

The object of this invention is therefore to provide polymers based on polymerisable DPP derivatives of improved photostability. They shall be better stabilised against, in particular, oxygen and UV radiation. Furthermore, this invention has for its object to provide also polymers and copolymers having improved photostable and processing properties (for example lower processing temperature).

The diketopyrrolopyrroles of formula I defined at the outset were accordingly found.

There was also found a process for the preparation of the diketopyrrolopyrroles I, their use for the preparation of polymers, polymers based on diketopyrrolopyrroles I, a process for their preparation, their use, coloured high molecular weight organic materials comprising the inventive polymers, a monomer mixture comprising the inventive diketopyrrolopyrroles I as well as the use of this monomer mixture.

According to this invention, $R_1$ is a radical of formula II

—Y—X—Z—Q    II, wherein Y is —$CR_3R_4$—, —$SO_2$—, —CO—, —Si(Hal)$_2$—, —POHal—, and $R_3$ and $R_4$ are each independently of the other hydrogen or $C_1$–$C_4$alkyl, typically methyl, ethyl, n-, i-propyl, n-, i-, sec- or tertbutyl, preferably methyl, and Hal is halogen, typically fluoro, chloro, bromo or iodo, preferably chloro; preferred are —$CH_2$—, —$CMe_2$—, —$SO_2$—, —CO—, —Si(Cl)$_2$—, —POCl—, particularly preferred are —$CH_2$—, —$SO_2$—, —CO—, —Si(Cl)$_2$—, very particularly preferred are —$CH_2$—, —$SO_2$—, —CO—, most preferred is —$CH_2$—.

According to this invention, X is an unsubstituted or substituted carbocylic or heterocyclic arylene group, preferably containing 6 to 14 carbon atoms, typically phenylene, naphthylene, anthracenylene, anthraquinonylene, pyridinylene, quinolinylene, preferably the group

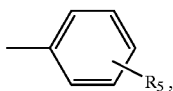

Wherein $R_5$ is a single bond in ortho-, meta- or para-position, or —O— in ortho-, meta- or para-position; paraphenylene and para-phenylenoxy are preferred and para-phenylenoxy is particularly preferred.

Z is a single bond, uninterrupted linear or branched (if there is more than one carbon atom) $C_1$–$C_{30}$alkylene, or linear or branched $C_2$–$C_{30}$alkylene which is interrupted once or more than once by a hetero atom, such as —O— or —S—, preferably —O—, —CH=CH—, —C≡C—, —N=CH—, —CH=N— or —NH—, or is $C_5$–$C_{12}$cycloalkylene.

$C_1$–$C_{30}$Alkylene embraces the linear as well as the branched representatives and can be, for example, —$CH_2$— and $C_2$–$C_{30}$alkylene, such as —$(CH_2)_2$—, —CH(Me)—, —$(CH_2)_3$—, —$CH_2$—CH(Me)—, —C(Me)$_2$—, —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$—, —$(CH_2)_{11}$—, —$(CH_2)_{12}$—, —$(CH_2)_{13}$—, —$(CH_2)_{14}$—, —$(CH_2)_{15}$—, —$(CH_2)_{16}$—, —$(CH_2)_{17}$—, —$(CH_2)_{18}$—, —$(CH_2)_{19}$—, —$(CH_2)_{20}$—, —$(CH_2)_{21}$—, —$(CH_2)22$—, —$(CH_2)_{23}$—, —$(CH_2)_{24}$—, —$(CH_2)_{25}$—, —$(CH_2)_{26}$—, —$(CH_2)_{27}$—, —$(CH_2)_{28}$—, $(CH_2)_{29}$—, —$(CH_2)_{30}$—, preferably —$CH_2$—, —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$—, —$(CH_2)_{11}$—, —$(CH_2)_{12}$—, —$(CH_2)_{13}$—, —$(CH_2)_{14}$—, —$(CH_2)_{15}$—, —$(CH_2)_{16}$—, —$(CH_2)_{17}$—, —$(CH_2)_{18}$—, —$(CH_2)_{19}$—, —$(CH_2)_{20}$— and also —CH($C_2$–$C_{30}$alkylene)— or, especially if $R_5$ is single bond in para-position, preferably —$CH_2$—, —$(CH_2)_2$—, and $C_{18}$–$C_{30}$alkylene, such as —$(CH_2)_{18}$—, —$(CH_2)_{19}$—, —$(CH_2)_{20}$—, —$(CH_2)_{21}$—, —$(CH_2)22$—, —$(CH_2)_{23}$—, —$(CH_2)_{24}$—, —$(CH_2)_{25}$—, —$(CH_2)_{26}$—, —$(CH_2)_{27}$—, —$(CH_2)_{28}$—, —$(CH_2)_{29}$—, —$(CH_2)_{30}$—.

In a preferred embodiment of this invention, Z is a single bond or a $C_2$–$C_{30}$alkylene chain which is interrupted several times by —O—, such as —$CH_2$—C(—)H—$CH_2$—O—$(CH_2)_p$—$CH_3$, wherein p is an integer such as 1, 2, 3, 4 or 5; —$CH_2$—C(—)H—$CH_2$—O—$(CH_2)_3$—$CH_3$ being particularly preferred.

Q is —OH, —SH, —$NH_2$, glycidyl, 1,2-epoxyethyl

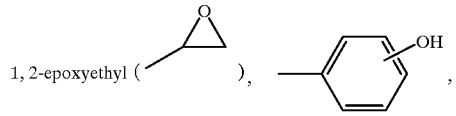

—CHO, —NCO, —CH=$CH_2$, —C($CH_3$)=$CH_2$, —OCO—CH=$CH_2$, —OCO—C(Me)=$CH_2$, —$CH_2$—CH=$CH_2$, —$CH_2$—OH, —CO—CH=$CH_2$, —CO—C($CH_3$)=$CH_2$, $C_5$–$C_7$cycloalkenyl,

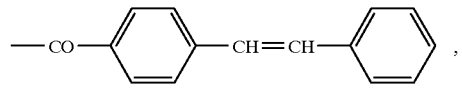

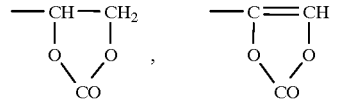

—CONH$R_6$, —COO$R_6$, —CO$R_6$, wherein $R_6$ is hydrogen or $C_1$–$C_6$-alkyl

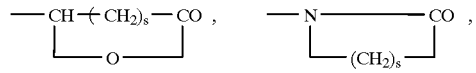

wherein s is an integer from 1 to 6; Q is preferably —OH, 1,2-epoxyethyl, —CH=$CH_2$, —C($CH_3$)=$CH_2$, —CO—CH=$CH_2$, —CO—C($CH_3$)=$CH_2$, —O—CO—CH=$CH_2$ or —O—CO—C($CH_3$)=$CH_2$, particularly preferably —OH, 1,2-epoxyethyl, —CH=$CH_2$, —C($CH_3$)=$CH_2$, —O—CO—CH=$CH_2$ and —O—CO—C($CH_3$)=$CH_2$.

According to this invention, $R_2$ is $C_1$–$C_6$alkyl,

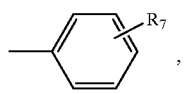

wherein $R_7$ is hydrogen or $C_1$–$C_6$alkyl, or is $R_1$; $C_1$–$C_6$alkyl and $R_1$ are preferred, and methyl and $R_1$ are particularly preferred.

A and B are each independently of the other a group of formula

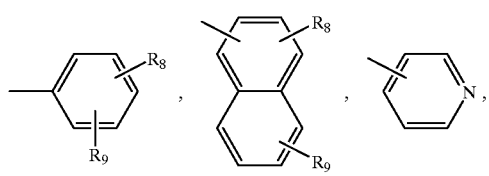

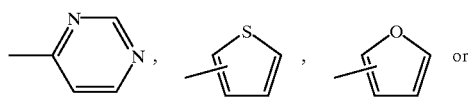

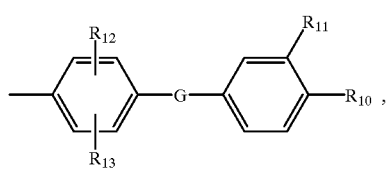

wherein $R_8$ and $R_9$ are each independently of the other hydrogen, halogen, $C_1$–$C_{18}$alkyl, $C_1$–$C_{18}$alkoxy, $C_1$–$C_{18}$alkylmercapto, $C_1$–$C_{18}$alkylamino, $C_1$–$C_{18}$alkoxycarbonyl, $C_1$–$C_{18}$alkylaminocarbonyl, —CN, —NO$_2$, trifluoromethyl, $C_5$–$C_6$cycloalkyl, —CH=N—($C_1$–$C_{18}$alkyl),

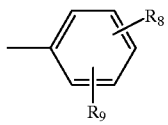

imidazolyl, pyrrazolyl, triazolyl, piperazinyl, pyrrolyl, oxazolyl, benzoxazolyl, benzothiazolyl, benzimidazolyl, morpholinyl, piperidinyl or pyrrolidinyl, and G is —CH$_2$—, —CH(CH$_3$)—, —C(CH$_3$)$_2$—, —CH=N—, —N=N—, —O—, —S—, —SO—, —SO$_2$—, —CONH— or —NR$_7$—, and $R_{10}$ and $R_{11}$ are each independently of the other hydrogen, halogen, $C_1$–$C_6$alkyl, $C_1$–$C_{18}$alkoxy or —CN, and $R_{12}$ and $R_{13}$ are each independently of the other hydrogen, halogen or $C_1$–$C_6$alkyl.

A and B are preferably each independently of the other a group of formula

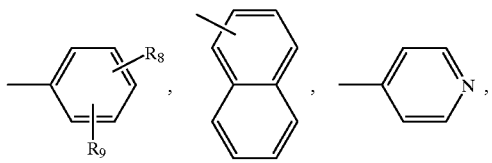

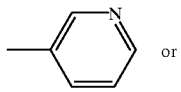

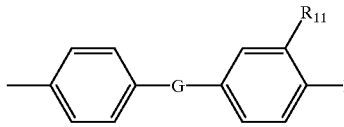

wherein $R_8$ and $R_9$ are each independently of the other hydrogen, halogen, such as chloro or bromo, $C_1$–$C_4$alkyl, $C_1$–$C_6$alkoxy, $C_1$–$C_6$alkylamino or CN, G is —O—, —NR$_7$—, —N=N— or —SO$_2$—, and $R_{10}$ and $R_{11}$ are hydrogen, $R_7$ is hydrogen, methyl or ethyl; A and B are particularly preferably identical and are a group of formula

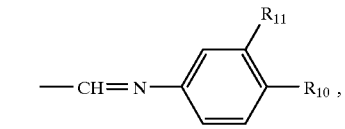

wherein $R_8$ and $R_9$ are each independently of the other hydrogen, methyl, tert-butyl, chloro, bromo or CN. $R_9$ is preferably hydrogen.

Halogen (or Hal) is usually iodo, fluoro, bromo or chloro, preferably bromo or chloro, particularly preferably chloro.

$C_1$–$C_4$Alkyl is usually methyl, ethyl, n-propyl, isopropyl, n-butyl, sec-butyl, i-butyl, tert-butyl;

$C_1$–$C_6$alkyl is typically methyl, ethyl, n-propyl, isopropyl, n-butyl, sec-butyl, i-butyl, tert-butyl, n-amyl, tert-amyl, hexyl;

the $C_1$–$C_{18}$alkyl radical is typically methyl, ethyl, n-propyl, isopropyl, n-butyl, sec-butyl, i-butyl, tert-butyl, n-amyl, tert-amyl, hexyl, heptyl, octyl, 2-ethylhexyl, nonyl, decyl, dodecyl, tetradecyl, hexadecyl or octadecyl;

$C_1$–$C_{18}$alkoxy is usually, and also in $C_1$–$C_{18}$alkoxycarbonyl, e.g. methoxy, ethoxy, n-propoxy, isopropoxy, butyloxy, hexyloxy, decyloxy, dodecyloxy, hexadecyloxy or octadecyloxy, preferably $C_1$–$C_6$alkoxy, such as methoxy, ethoxy, n-propoxy, isopropoxy, butyloxy, hexyloxy;

$C_1$–$C_{18}$ alkylmercapto is, for example, methylmercapto, ethylmercapto, propylmercapto, butylmercapto, octylmercapto, decymercapto, hexadecylmercapto or octadecylmercapto; $C_1$–$C_{18}$alkylamino is, also in $C_1$–$C_{18}$alkylaminocarbonyl, e.g. methylamino, ethylamino, propylamino, hexylamino, decylamino, hexadecylamino or octadecylamin, preferably $C_1$–$C_6$-alkylamine, such as methylamino, ethylamino, n-propylamino, hexylamino.

$C_5$–$C_6$Cycloalkyl is, for example, cyclopentyl or cyclohexyl, preferably cyclohexyl.

$C_5$–$C_7$Cycloalkenyl is usually mono- or bicyclic cycloalkenyl, such as cyclopentenyl, cyclohexenyl or norbornenyl.

Preferred DPP derivatives of formula I are those, wherein $R_1$ is —$CH_2$—(para-phenylene)—O—Z—Q or —CO—(para-phenylene)—O—Z—Q, and $R_2$ is methyl or $R_1$. A, B, Z and Q are in the preferred case the preferred radicals defined above, particularly preferred radicals being: —$CH_2$—Ph—$NH_2$, —CO—Ph—$NH_2$, —$CH_2$—Ph—SH, —CO—Ph—SH, —$CH_2$—Ph—NCO, —CO—Ph—NCO, —$SO_2$—Ph—NCO, —$CH_2$—Ph—COOH, —$CH_2$—Ph—COOMe, —$CH_2$—Ph—CHO, —$CH_2$—Ph—$CH_2OH$, wherein Ph is 1,4-phenylene. These radicals may be modified by known measures by chain prolongation, especially if one wishes to increase their solubility.

Other preferred DPP derivatives of formula I are those, wherein $R_1$ is —$CH_2$—(para-phenylene)—Z—Q or —CO—(para-phenylene)—Z—Q, wherein Z is $C_1$–$C_{30}$alkylene, particularly preferably $C_1$–$C_2$— and $C_{18}$–$C_{30}$alkylene, and $R_2$ and Q are the radicals defined above, preferably the preferred radicals.

Very particularly preferred DPP derivatives I are:

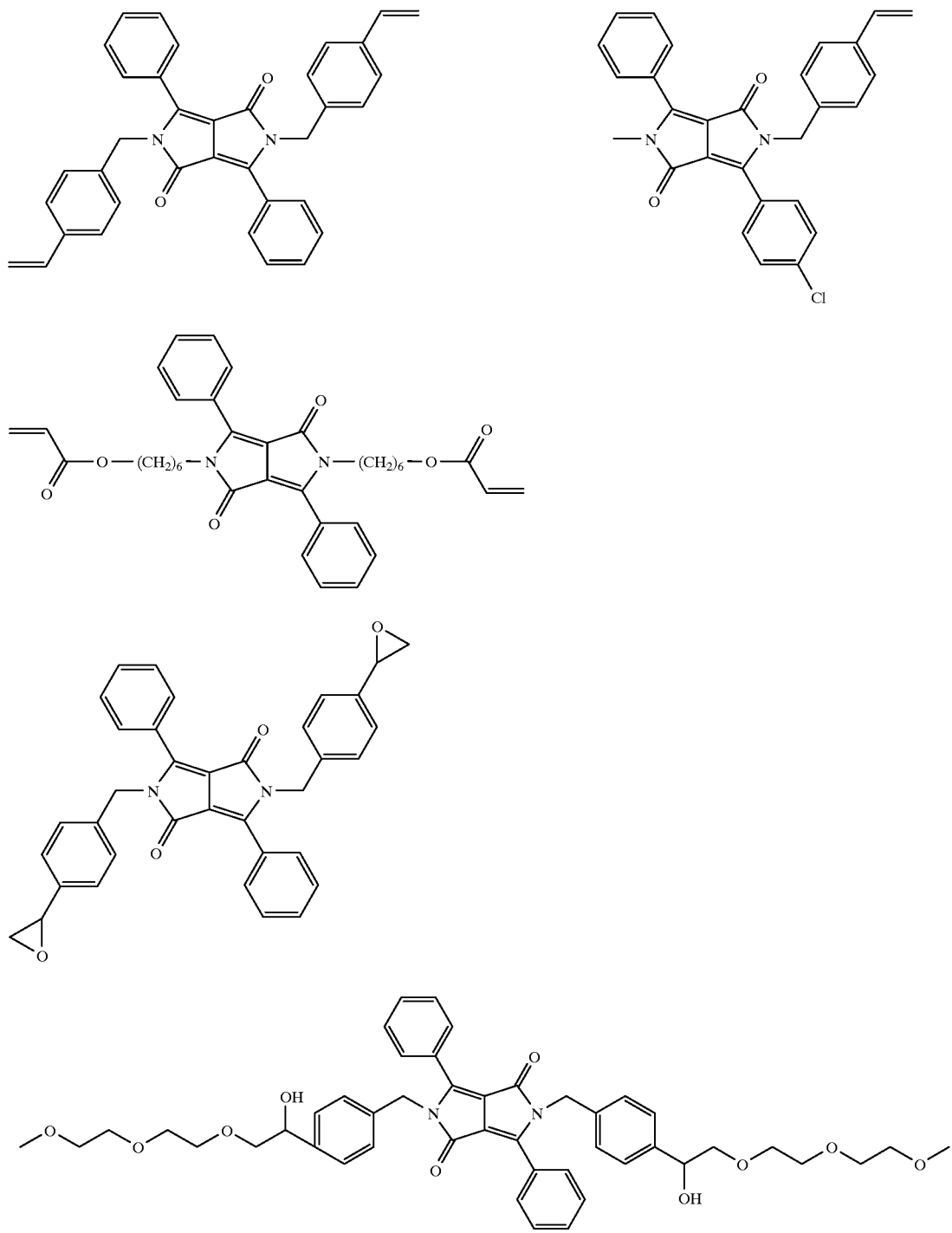

-continued

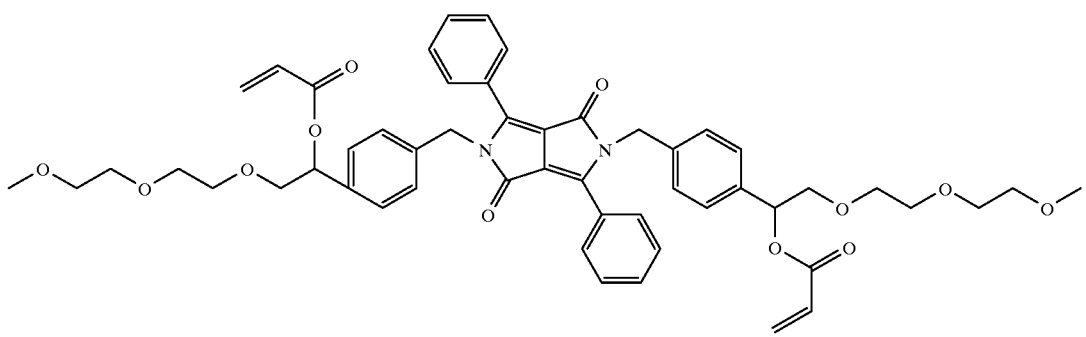

Another embodiment of this invention relates to a process for the preparation of the inventive DPP derivatives I, which comprises reacting the DPP derivatives of formula III

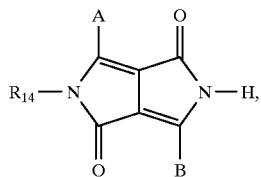

wherein $R_{14}$ is hydrogen or $R_2$, which DPP derivatives are preferably unsubstituted or monosubstituted at the nitrogen atoms,
with halogenated compounds of formula IV

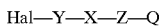

in the presence of a base.

If $R_{14}$ is $R_2$, then the molar ratio of DPP III to the halogen compound IV is conveniently chosen to be in the range from 2:1 to 0.9:1, preferably from 2:1 to 1.1:1, particularly preferably from 1.5:1 to 1.3:1 and, if $R_{14}$ is hydrogen, in the range from 4:1 to 1.8:1, preferably from 4:1 to 2.2:1, particularly preferably from 3:1 to 2.6:1.

The DPP III compound can be prepared, for example, by reacting a pyrrolinone with a nitrile (see also the reaction of pyrrolinone IX with nitrile X hereinbelow). The compound IIIa in particular, wherein $R_{14}$ is hydrogen, is obtainable e.g. by the process described in U.S. Pat. No. 4,579,949.

The base employed is usually an alkali metal carbonate or alkaline earth metal carbonate, such as sodium carbonate, potassium carbonate, a hydride, in particular an alkali metal hydride such as sodium hydride or potassium hydride, or a $C_1$–$C_4$alcoholate, such as the corresponding sodium and potassium salts of methanol, ethanol, n-, i-propanol, n-, i-, sec- or tert-butanol, typically potassium methanolate, sodium methanolate, sodium ethanolate, potassium ethanolate. The alkali metal carbonates are preferred, in particular the potassium carbonate.

The amount of base is usually chosen as a function of the chosen base, for example in the range from 4:1 to 1.1:1, based on DPP III, if $R_{14}$ is $R_2$, and normally using twice the amount of the base if $R_{14}$ is hydrogen.

The reaction temperature usually depends on the kind of substances used, such as on the choice of the base. For example, when using potassium carbonate, it is usual to choose a temperature in the range from 25 to 150° C., e.g. preferably from 70 to 150, particularly preferably from 70 to 140° C., it being possible to choose other temperature ranges depending on the educts used.

The reaction is preferably carried out in an aprotic polar solvent such as dimethylformamide (DMF), dimethylsulfoxide (DMSO), dimethylacetamide (DMAC). DMF is preferred. The solvent is normally used in excess, based on the DPP III, preferably in 10- to 50-fold excess.

The DPP I is preferably precipitated from the reaction mixture using water or an alcohol and is recrystallised or concentrated to dryness and then recrystallised.

It has also been found that it is possible to react, in a first step, the DPP derivatives of formula III with the group

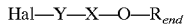

and then, in a second reaction step, to convert the group —$OR_{end}$ to a —OH group (depending on the choice of X, the —OH group may be in terminal position unless X is a branched alkyl radical which may be interrupted by hetero atoms, in particular —O—) and, in a third step, to further react this phenolic end group with an epoxide to the DPP I of this invention. In a preferred embodiment of this invention, and especially if one wishes to photochemically polymerise the inventive DPP I, the —OH group or groups are reacted with acrylic acid chloride or methacrylic acid chloride to the corresponding acrylates or methacrylates.

According to findings so far, the choice of $R_{end}$ is not relevant for the success of the reaction. It is preferred, however, to choose a suitable leaving group for $R_{end}$, particularly preferably a $C_1$–$C_4$alkyl group, in particular methyl.

The epoxide chosen is usually a terminal epoxide with a $C_3$–$C_{30}$alkyl chain which is uninterrupted or interrupted once or more than once, for example

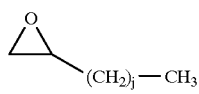

or

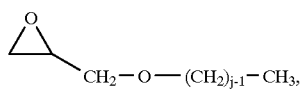

wherein j may be an integer from 0 to 27. Butyl glycidyl ether may be mentioned as example.

The reaction with the halogen compound Hal—Y—X—O—$R_{end}$ is usually carried out in a manner analogous to the reaction with halide IV described above.

The conversion of the —$OR_{end}$ group into the —OH group is usually carried out by the method described in Tetrahedron Letters 21 (1980) 2305 by reacting it with a silane, such as phenylthiotrimethylsilane.

In some cases the phenolic group can also be introduced directly by means of Hal—Y—X—OH, for example when Y=CH$_2$—, —SO$_2$—, —CO—, —CMe$_2$—.

The reaction of a phenol with an epoxide is known and can be carried out, for example, by the method described in Houben-Weyl, Vol. 6/3, page 456 et seq. (1987).

The —CH$_2$phenylene unit can be introduced, for example, via a corresponding halohydroxy compound by the method described in Houben-Weyl, Vol. 11/1, p. 42 et seq. (1987). The starting compound is accessible, for example, via halogenation of a dihydroxy compound such as 1,4-di (hydroxymethyl)phenylene, e.g. with sulfonyl chloride (see J.Org.Chem., p. 444–450 (1966)). After the reaction with DPP III, the alcoholic groups can be used for introducing polymerisable groups, such as the acrylate or methacrylate group, or for chain prolongation, for example by reaction with an epoxide (see above).

Where a reaction of the alcoholic DPP derivative I with an acrylic acid chloride or methacrylic acid chloride is desired, it may be carried out e.g. by the method described in Houben-Weyl, Vol. 8, p. 543 et seq. (1987). In a preferred embodiment of this invention, a basic binder is used to remove the released hydrogen chloride or part thereof from the reaction mixture. Preferred basic binders are, for example, amines, particularly preferably secondary amines, very particularly preferably thiodiphenylamine (=phenothiazine).

If —Z—Q is an oxyalkylene radical, then the corresponding DPP derivatives I may be obtained, for example, by reacting epichlorhydrin with an oxyalkanol such as CH$_3$— (OCH$_2$CH$_2$)$_k$—OH (wherein k is e.g. 3, 4, 5, 6 or 7) to the corresponding epoxide and then continuing as described. Long oxyalkylene radicals in particular, i.e. k$\geq$3, preferably 3$\leq$k$\leq$7, generally improve the processability of the novel polymers.

The novel DPP I can usually be modified by chain prolongation, in particular if Q is a radical selected from the group consisting of —OH, 1,2-epoxyethyl, —SH, —NH$_2$, —NCO, —COOH, —CH$_2$OH, —CH$_2$—CH=CH$_2$ and —CHO. Thus it is possible to react the —OH, —CH$_2$OH and —SH group with an epoxide and then to react the newly formed —OH group, if desired, with acrylic acid chloride or methacrylic acid chloride to the corresponding acrylic acid or methacrylic acid derivatives. The —NH$_2$ radical can be reacted, for example, with isocyanatoethylmethacrylate to —NHCO—CH$_2$—CH$_2$—O—C(O)—C(Me)=CH$_2$. The NCO radical can be reacted, for example, with hydroxyethylmethacrylate to —NHCO—CH$_2$—CH$_2$—O—C(O)—C (Me)=CH$_2$. The COOH group can be modified, for example, with isocyanatoethylmethacrylate to —COO—NHCO—CH$_2$—CH$_2$—O—C(O)—C(Me)=CH$_2$. An allyl group can be reacted, for example, with a thiol such as HS—(CH$_2$)$_6$—NH$_2$ or HS—(CH$_2$)$_2$—O—(CH$_2$)$_2$—O—(CH$_2$)$_2$—OH to —(CH$_2$)$_3$—S—(CH$_2$)$_6$—NH$_2$ or —(CH$_2$)$_3$—S—(CH$_2$)$_2$—O—(CH$_2$)$_2$—O—(CH$_2$)$_2$—OH. An aldehyde group, —CHO, can be reacted with a primary amine such as H$_2$N—CH$_2$—CH$_2$—O—CH$_2$—CH$_2$—OH to —CH=N—CH$_2$—CH$_2$—O—CH$_2$—CH$_2$—CH$_2$—OH. The 1,2-epoxyethyl group or glycidyl can be derivatised by reaction with an alcohol in a manner known per se, for example by catalysis with Sn(BF$_4$)$_2$.

A particular embodiment of this invention relates to the reaction of the DPP derivative III with a halogenated compound IV in the manner described above, wherein Q is the 1,2-epoxy group. Hal—Y—X—Z—Q is particularly preferably Cl—CH$_2$—(paraphenylene)—(1,2-epoxyethyl). Epoxy-substituted DPP I are thus accessible which can be further derivatised, e.g. by reaction with a compound carrying a OH group (see above). The resulting DPP I carrying OH groups can also be further reacted as indicated above, in particular with acrylic acid chloride or methacrylic acid chloride to the corresponding acrylates and methacrylates.

The epoxy compounds are generally obtainable by generally known methods from the corresponding compounds, which contain a double bond, by reaction with a peracid or perester, typically with peracetic acid.

It may also be mentioned that opening an epoxy ring by reaction with an alcohol as described above may produce isomers, so that this invention also embraces isomer mixtures such as the corresponding secondary and primary alcohols:

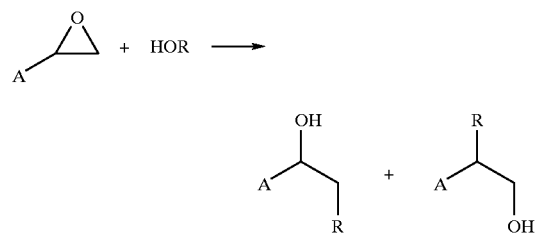

Optical isomers may also be obtained, for example in the form of a racemate mixture, which this invention also embraces.

Another embodiment of this invention relates to the use of the diketopyrrolopyrroles I for the preparation of polymers.

The polymerisation of the inventive DPP I is usually carried out in a manner known per se, if desired in the presence of a suitable, preferably customary, comonomer carrying e.g. at least one carbon-carbon double bond or of a polymer carrying polyreactive groups.

In a preferred embodiment of this invention, coloured (co-)polymers can be prepared by polyreacting a mixture consisting of novel DPP monomers and other customary and suitable copolymerisable monomers in liquid phase such as in a melt, solution, suspension and emulsion.

Suitable copolymerisable monomers to be mentioned are, for example, the group of the acrylates, methacrylates and other customary vinylic monomers such as styrene and its customary monomer derivatives or 2-N-vinylpyrrolidone. Particularly preferred acrylates are monofunctional acrylates such as butanediolmonoacrylate, 2-hydroxyethylacrylate, butylacrylate, 2-ethylhexylacrylate, phenoxyethylacrylate, tetrahydrofurfurylacrylate, polypropylene glycol monoacrylate, bifunctional acrylates such as 1,6-hexanedioldiacrylate, tripropylene glycol diacrylate, polyethylene glycol(200) diacrylate and polyethylene glycol (400) diacrylate, ethoxylated and propoxylated neopentyl glycol diacrylate, polyfunctional acrylates such as trimethylolpropanetriacrylate, pentaerythritoltriacrylate, ethoxylated or propoxylated trimethylolpropanetriacrylate, propoxylated glycerol triacrylate, tris(2-hydroxyethyl) isocyanuratetriacrylate as well as their mixtures with one another. Such compounds are sufficiently known from, inter alia, "Strahlenhärtung", Curt R. Vincentzu Verlag, Hannover, p. 83 to 92 (1996).

These novel DPP polymers are usually prepared by commonly known methods, e.g. either by a polyreaction, i.e. by polymerisation (thermal or photochemical), polycondensation or polyaddition, or by a polymer-analogous reaction, i.e. by reacting the novel DPP compounds containing suitable reactive groups with polymers already obtained which in turn contain reac-tive groups (grafting). Photochemical polymerisation is preferred, especially if Q is an acrylic or methacrylic radical.

According to findings to date, all known kinds of polyreactions can be carried out with the novel DPP compounds (DPP monomers). It is thus possible to prepare e.g. vinyl polymers, allyl polymers, vinyl ester polymers, vinylamide polymers, vinyl acetate polymers or vinyl ketone polymers from DPP monomers, the reactive groups of which contain C=C bonds; polyaldehydes, polyisocyanates, polyepoxides, polyethers, polyacetones or polylactams from monofunctional DPP monomers, the reactive groups of which contain hetero atoms; and from bifunctional DPP monomers, the reactive groups of which contain hetero atoms, via polycondensation polyesters, polyamides, polyimides or polycarbonates and, via polyaddition, polyepoxides, polyurethanes or polyimides, the polymerisation being, for example, a radical, cationic or anionic polymerisation, coordination polymerisation or group transfer polymerisation.

Typical examples of the preparation of DPP polymers, starting from the novel DPP monomers I, are (a) the polymerisation for the preparation of DPP polyacrylates or polymethacrylates by radical thermal polymerisation of DPP acrylates or DPP methacrylates, i.e. DPP I, wherein Q is an acrylic or methacrylic group, or the radical photopolymerisation of DPP acrylates or DPP methacrylates, (b) the polycondensation for the preparation of DPP-containing polyesters from DPP I monomers, wherein Q is a hydroxy group and diacid chlorides, or the preparation of DPP polycarbonates from DPP diols and phosgene, (c) the polyaddition for the preparation of DPP polyurethanes from DPP diols and diisocyanates, or the preparation of DPP polyepoxides from DPP epoxides and amines, and also (d) the polymer-analogous reaction, e.g. the reaction of a DPP alcohol with a polymer prepared from styrene and maleic acid anhydride, which thus contains anhydride groups, to a polymer containing DPP mono- or diester groups.

Where required, the novel DPP polymers also contain additives, such as light stabilisers, antioxidants and UV absorbers, which may be added during or after the actual polymerisation, e.g. also during the processing of the polymers (extrusion). These additives can themselves also contain polyreactive groups and can in this case be copolymerised together with the DPP monomers I.

The actual preparation of polymers is known from the state of the art (described, inter alia, in Houben-Weyl "Methoden der Organischen Chemie", "Makromolekulare Stoffe", Vol. E20, parts 1–3 (1986,1987)).

If Q is the —CH=CH$_2$—, acrylate or methacrylate group, the polymerisation can be carried out e.g. photochemically, one of the customary photoinitiators (see e.g. "Chemistry & Technology of UV & EB Formulations for Coatings, Inks and Paints, Vol. 3: Photoinitiators for Free Radical and Cationic Polymerization" 1991, p. 1115–325) usually being added to the reaction mixture in an amount in the range from typically 0.5 to 5% by weight, based on the sum of all monomers used.

Moulded articles of all kinds, coatings and relief images or relief structures may be prepared from the novel monomeric DPP I by action of actinic radiation. The actinic radiation can range from γ-radiation to the near UV range. The radiation used usually depends essentially on the absorption of the photoinitiators employed. It is preferred to use electromagnetic radiation from the UV to the visible range. Suitable radiation sources are known. These may be, for example, lamps or lasers. UV lamps (mercury lamps) or UV lasers are preferred. The irradiation time usually depends, inter alia, on the kind of light source used and can range from hours to minutes or even seconds. The novel monomeric DPP I are particularly preferably used to prepare polymeric films, it being possible for the coating layer to be in the range from 5 to 500 μm depending on the end use requirement.

Another preferred embodiment of this invention thus relates to polymers based on the diketopyrrolopyrroles I according to claim 1, which are obtainable by polyreacting at least one diketopyrrolopyrrole I according to claim 1 or a mixture consisting of
(A) from 0.5 to 20, preferably from 1 to 10% by weight, based on the sum of the components (A) and (B), of a mixture consisting of
(a) from 100 to 1, preferably from 95 to 20, particularly preferably from 90 to 40% by weight, based on the sum of the components (a) and (b), of a diketopyrrolopyrrole I,
(b) from 0 to 99, preferably from 5 to 80, particularly preferably from 10 to 60% by weight,
based on the sum of the components (a) and (b), of the diketopyrrolopyrrole of formula V,

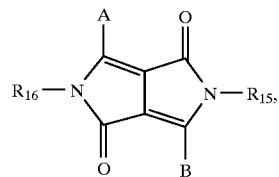

wherein A and B are as defined in claim 1,
R$_{15}$ is a radical containing a polyreactive group, and
R$_{16}$ is C$_1$–C$_6$alkyl,

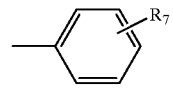

or R$_{15}$, and
(B) from 99.5 to 80, preferably from 99 to 90% by weight, based on the sum of the components (A) and (B), of a monomer which is copolymerisable with the diketopyrrolopyrroles I and V,
the sums of (A) and (B) and of (a) and (b) each making up 100% by weight.

Another preferred embodiment of this invention relates to a process for the preparation of these inventive polymers, which comprises polyreacting at least one diketopyrrolopyrrole I according to claim 1 or a mixture consisting of
(A) from 0.5 to 20, preferably from 1 to 10% by weight, based on the sum of the components (A) and (B), of a mixture consisting of
(a) from 100 to 1, preferably from 95 to 20, particularly preferably from 90 to 40% by weight, based on the sum of the components (a) and (b), of a diketopyrrolopyrrole I,
(b) from 0 to 99, preferably from 5 to 80, particularly preferably from 10 to 60% by weight,
based on the sum of the components (a) and (b), of the diketopyrrolopyrrole of formula V, as defined above, and
(B) from 99.5 to 80, preferably from 99 to 90% by weight, based on the sum of the components (A) and (B), of a monomer which is copolymerisable with the diketopyrrolopyrroles I and V, the sums of (A) and (B) and of (a) and (b) each making up 100% by weight, in analogy to the polyreaction described above.

Another embodiment of this invention relates to mixtures consisting of (A) from 0.5 to 20, preferably from 1 to 10% by weight, based on the sum of the components (A) and (B), of a mixture consisting of
  (a) from 100 to 1, preferably from 95 to 20, particularly preferably from 90 to 40% by weight, based on the sum of the components (a) and (b), of a diketopyrrolopyrrole I,
  (b) from 0 to 99, preferably from 5 to 80, particularly preferably from 10 to 60% by weight, based on the sum of the components (a) and (b), of the diketopyrrolopyrrole of formula V, as defined above, and (B) from 99.5 to 80, preferably from 99 to 90% by weight, based on the sum of the components (A) and (B), of a monomer which is copolymerisable with the diketopyrrolopyrroles I and V, the sums of (A) and (B) and of (a) and (b) each making up 100% by weight.

Polyreactive groups are understood to be, for example, polymerisable groups, such as acrylate radicals, or polycondensable groups, such as hydroxy chloride or acid chloride groups, or also groups capable of polyaddition, such as epoxy, hydroxy or isocyanate groups.

$R_{15}$ is preferably a radical of formula VI $$-(CH_2)_m-CH=CH-(CH_2)_n-CH_3 \quad (VI)$$

or $$-(L)_t-U-(W)_v-Q \quad (VII),$$

wherein m and n are each independently of the other an integer from 0 to 12, for example 0, 1, 2, 3, 4, 5, 6, 7, 8, 9, 10, 11, 12, and m and n are preferably chosen such that the sum of m+n is at least 4, and t and v are each independently of the other 0 or 1, $R_{15}$ of formula VII particularly preferably being $-(CH_2)_n-O-CO-CH=CH_2$, wherein $n \geq 4$, n preferably being an integer from 4 to 6, in particular 6, and $-(CH_2-CH_2-O)_m-CO-CH=CH_2$, wherein m=1, 2, 3, 4, 5, preferably 2, U is $C_2-C_{18}$alkylene which is uninterrupted or interrupted once or more than once by —O— and/or —S—, —NH—, phenylene, —COO—, —CONH—,

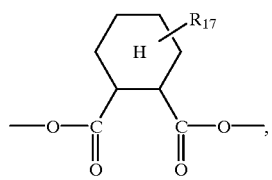

wherein $R_{17}$ is hydrogen or methyl, interrupted $C_2-C_{18}$alkylene, preferably $C_4-C_{18}$alkylene, L is

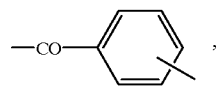

—Si(Hal)$_2$—, —Si(OC$_2$H$_5$)$_2$—, —Si(OCOCH$_3$)$_2$—, —CH$_2$—CH(OH)— or —CH(CN)—, and W is —O—, —NH—, —COO—, phenylene,

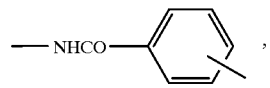

preferably para-substituted, —Si(Hal)$_2$—, —Si(OC$_2$H$_5$)$_2$—, —Si(OCOCH$_3$)$_2$—, wherein Hal has the meaning given above, preferably chloro, and Q is as defined above, the substituents of the compounds of formula V being chosen such that the compounds of formula I and of formula V are different.

Particularly important diketopyrrolopyrroles are those of formula V, wherein $R_{15}$ is a radical of formula VII $$-U-(O)_v-Q \quad (VIII),$$

wherein

U is $C_4-C_{12}$alkylene which is uninterrupted or interrupted 1, 2 or 3 times by —O— and/or once by —S—, —NH—,

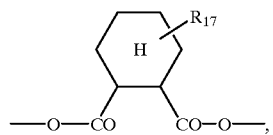

v and $R_{17}$ have the meanings given above, and

Q is —OH; —CH=CH$_2$, —C(CH$_3$)=CH$_2$, —CO—CH=CH$_2$ or —CO—C(CH$_3$)=CH$_2$.

U is preferably —(CH$_2$)$_q$—, wherein q may be an integer from 6 to 12, such as 6, 7, 8, 9, 10, 11 and 12, —(CH$_2$CH$_2$O)$_2$—CH$_2$CH$_2$— or

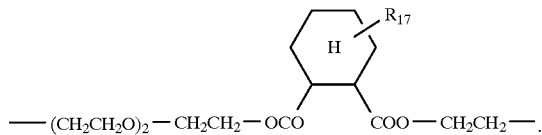

$R_{16}$ is preferably CH$_3$ or $R_{15}$ and the same preferred meanings apply as for $R_{15}$.

The diketopyrrolopyrroles of formula V, wherein $R_{15}$ is a radical of formula VI or VII, and $R_{16}$ is $C_1-C_6$alkyl or

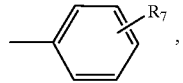

are preferably prepared by reacting a pyrrolinone of formula

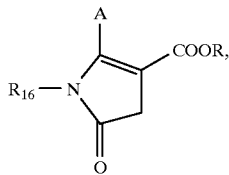

IX wherein R is usually chosen such as to form a standard leaving group ROH, wherein R is preferably $C_1$–$C_4$alkyl, with a nitrile of formula X, B—CN, wherein A and B have the meanings given above, resulting in the diketopyrrolopyrrole of formula

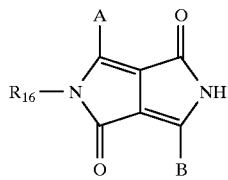

and subsequently reacting the latter with a compound of formula XI, i.e. $R_{15}$Hal, or, if L in the radical of formula VII is —$CH_2$—CH(OH)—, with a compound of formula XII

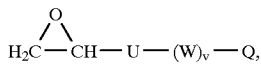

XII wherein $R_{16}$, U, W, Q and v have the meanings given above and Hal is preferably chloro or bromo.

The reaction conditions such as the ratio of the educts to each other, the temperature etc. can be chosen, for example, in analogy to the process described in U.S. Pat. No. 4,778,899, so that further details may be dispensed with here.

In general analogy, diketopyrroles of formula V, wherein $R_{15}$ and $R_{16}$ are identical, are obtained in a preferred embodiment of this invention starting from a diketopyrrolopyrrole of formula

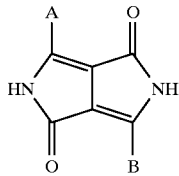

IIIa (e.g. obtainable by the process described in U.S. Pat. No. 4,579,949), using corresponding amounts of the compounds of formula XI or XII.

In another preferred embodiment of this invention, diketopyrrolopyrroles of formula V, wherein Q is, for example, —CO—CH=$CH_2$ or —CO—C($CH_3$)=$CH_2$ and v is 1, can be prepared by reacting diketopyrrolopyrroles of formula V, wherein Q is —OH, with acrylic acid chloride or methacrylic acid chloride. In general analogy it is also possible to introduce e.g. the groups —Si(Cl)$_2$—CH=$CH_2$, —Si(O$C_2H_5$)$_2$—CH=$CH_2$, —Si(OCO$CH_3$)$_2$—CH=$CH_2$, —CONH$R_6$, —COO$R_6$ etc. as Q or W—Q.

Pyrrolinones of formula IX are usually obtained by methods known per se, for example by cyclising a compound of formula

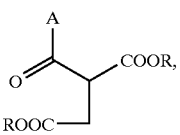

XIII wherein A and R have the meanings given above, with an ammonium salt to the pyrrolinone of formula

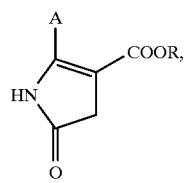

as described in U.S. Pat. No. 4,778,899, and by further reaction with a compound of formula $R_{16}$Hal, wherein $R_{16}$ is $C_1$–$C_6$alkyl or

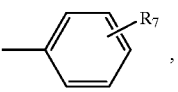

using commonly known methods.

The compounds of formulae X, XI, XII, IIIa and XIII are known and/or can be prepared in analogy to commonly known processes. Another embodiment of this invention relates to the use of the novel mixture for the preparation of polymers.

In another of its aspects, this invention relates to the use of polymers prepared according to this invention for colouring high molecular weight organic materials, for formulations of decorative cosmetics, for the production of inks, printing inks, paint systems, in particular automotive lacquers and photosensitive coatings, photo- and electroconducting polymers, fluorescent brighteners, photocell aggregates, coloured photoresists and dispersion paints.

The DPP polymers prepared according to this invention are particularly suitable for colouring high molecular weight organic materials, such as biopolymers, plastic materials, including fibres, glasses, ceramic products, for formulations of decorative cosmetics, for the preparation of inks, printing inks, paint systems, in particular automotive lacquers and photosensitive coatings, photo- and electroconducting polymers, fluorescent brighteners, photocell aggregates, coloured photoresists and dispersion paints, and the diketopyrrolopyrroles of this invention can also be used in the biomedical field, for example for the preparation of diagnostic agents, and in the fields of impact and non impact printing and photo/repro in general.

Illustrative examples of suitable high molecular weight organic materials which can be coloured with the novel DPP polymers, are vinyl polymers, such as polystyrene, poly-α-methylstyrene, poly-p-methylstyrene, poly-p-hydroxystyrene, poly-p-hydroxyphenylstyrene, polymethyl methacrylate and polyacrylamide as well as the corresponding methacrylic compounds, polymethylmaleate, polyacrylonitrile, polymethacrylonitrile, polyvinyl chloride, polyvinyl fluoride, polyvinylidene chloride, polyvinylidene fluoride, polyvinyl acetate, polymethylvinyl ether and polybutyl vinyl ether; polymers derived from maleinimide and/or maleic anhydride, such as copolymers of maleic anhydride with styrene; polyvinyl pyrrolidone; ABS; ASA; polyamides; polyimides; polyamidimides; polysulfones; polyether sulfones; polyphenylene oxides; polyurethane; polyureas; polycarbonates; polyarylenes; polyarylenesulfides; polyepoxides; polyolefins, such as polyethylene and polypropylene; polyalkadienes; biopolymers and their derivatives, such as cellulose, cellulose ethers and cellulose esters, such as ethylcellulose, nitrocellulose, cellulose acetate and cellulose butyrate, starch, chitin, chitosan, gelatin, zein; natural resins; synthetic resins, such as alkyd resins, acrylic resins, phenolic resins, epoxy resins, aminoformaldehyde resins, such as urea/formaldehyde resins and melamine/formaldehyde resins; rubber; casein; silicone and silicone resins; caoutchouc, chlorinated rubber; and also polymers which are used, for example, as binders in paint systems, such as novolaks derived from $C_1$–$C_6$aldehydes, such as formaldehyde and acetaldehyde and a binuclear or mononuclear, preferably mononuclear, phenol which, if desired, is substituted by one or two $C_1$–$C_9$alkyl groups, one or two halogen atoms or a phenyl ring, such as o-, m- or p-cresol, xylene, p-tert-butylphenol, o-, m- or p-nonylphenol, p-chlorophenol or p-phenylphenol, or from a compound containing more than one phenolic group, typically resorcinol, bis(4-hydroxyphenyl)methane or 2,2-bis(4-hydroxyphenyl)propane; as well as suitable mixtures of the cited materials.

Particularly preferred high molecular weight organic materials, in particular for the preparation of a paint system, printing ink or ink, are e.g. cellulose ethers and cellulose esters, such as ethylcellulose, nitrocellulose, cellulose acetate and cellulose butyrate, natural resins or synthetic resins (polymerisation or condensation resins), such as aminoplasts, in particular urea/formaldehyde resins and melamine/formaldehyde resins, alkyd resins, phenolic plastics, polycarbonates, polyolefins, polystyrene, polyvinyl chloride, polyamides, polyurethanes, polyesters, ABS, ASA, polyphenylene oxides, rubber, casein, silicone and silicone resins as well as their possible mixtures with one another.

It is also possible to use high molecular weight organic materials in dissolved form as film formers, such as boiled linseed oil, nitrocellulose, alkyd resins, phenolic resins, melamine/formaldehyde resins and urea/formaldehyde resins and also acrylic resins.

The cited high molecular weight organic compounds can be used singly or in mixtures, e.g. as granulates, plastic compounds, melts or in the form of solutions, in particular for the preparation of spinning solutions, paint systems, coating compositions, inks or printing inks.

In a preferred embodiment of this invention, the novel DPP polymers are used for mass colouring polyvinyl chloride, polyamides and; in particular, polyolefins such as polyethylene and polypropylene, and for the preparation of paint systems, including powder coatings, inks, printing inks and paints. Examples of preferred binders for paint systems to be mentioned are alkyd/melamine surface coating resins, acryl/melamine surface coating resins, cellulose acetate/cellulose butyrate paints and two-component paints based on acrylic resins crosslinkable with polyisocyanate.

According to findings so far, the novel DPP polymers can be added to the material to be coloured in any desired amount, depending on the end use requirements. In the case of high molecular weight organic materials, for example, the novel DDP polymers can be used in amounts in the range from 0.01 to 40, preferably from 0.1 to 20% by weight, based on the total weight of the high molecular weight organic material.

The high molecular weight organic materials are normally coloured with the novel DPP polymers such that said polymers, if desired in the form of masterbatches, are admixed to the high molecular weight organic materials using customary suitable appliances, for example extruders, roll mills, mixing or milling apparatus. The material thus treated is then usually brought into the desired final form by methods known per se, such as calendering, moulding, extruding, coating, casting or injection moulding.

In a particularly preferred embodiment of this invention, it is possible to dissolve DDP I containing photocurable groups such as acrylate or methacrylate groups, or also mixtures of the above kind of DPP I with DPP V, in other photocurable monomers, either with or without solvent, in the latter case e.g. by melting and dissolving, and then to mix them with corresponding photoinitiators and to coat suitable substrates therewith, the coatings being cured, i.e. polymerised, by means of actinic radiation, preferably UV radiation.

In another preferred embodiment of this invention, the novel DPP monomers can be polyreacted in an extruder together with other monomers, in particular those customarily used for the preparation of the above-mentioned polymers (reactive extrusion, in analogy to the process described, inter alia, in EP-A 337 951). Copolymers prepared in this manner usually have the same spectrum of use as the blends of novel DPP polymers and high molecular weight organic materials mentioned so far.

To produce non-brittle mouldings or to reduce their brittleness, so-called plasticisers may be added to the high molecular weight substances prior to moulding. These plasticisers may be, for example: the esters of phosphoric acid, phthalic acid and sebacic acid. The plasticisers can be added before, during or after colouring the high molecular weight substances with the novel DPP polymers.

To obtain different shades, the novel DPP polymers can be advantageously added in admixture with fillers, transparent and opaque white, coloured and/or black pigments and conventional luster pigments in the desired amount.

To prepare paint systems, coating compositions, inks and printing inks, the corresponding high molecular weight organic substances, such as binders, synthetic resin dispersions and the like, and the novel DPP polymers, are usually dispersed or dissolved, if desired together with customary additives, such as fillers, paint auxiliaries, siccatives, plasticisers and/or additional pigments, in a shared solvent or solvent mixture. This may be effected by dispersing or dissolving the individual components by themselves or also several together and only then bringing all the components together, or by adding all of them in one go.

For printing applications, all conventional industrial printing methods may be used, such as screen printing, rotogravure, bronze printing, flexographic printing and offset printing.

This invention accordingly relates in another of its embodiments to coloured high molecular weight organic materials prepared by using the polymers according to this invention, to formulations of decorative cosmetics, inks, printing inks, paint systems, in particular automotive lacquers and photosensitive coatings, photo- and electroconducting polymers, fluorescent brighteners, photocell aggregates, coloured photoresists and dispersion paints, preferably to coloured high molecular weight organic materials and paint systems, particularly preferably to automotive paints and photosensitive coatings. The polymers and copolymers prepared according to this invention based on the novel DPP monomers I have improved photostability compared to the corresponding polymers of the state of the art.

EXAMPLES

Example 1

14.42 g (0.05 mol) of the DPP derivative Pigment Red 3067E (obtainable according to Example 1 of U.S. Pat. No.

4,579,949) and 0.12 g (0.5% in p-vinylbenzyl chloride ("VBC")) of hydroquinone are heated, with stirring, in 180 ml of dimethylformamide ("DMF") under nitrogen to a temperature in the range from 120–125° C. 20.73 g (0.150 mol) of potassium carbonate, dried at 250° C., are added to the resulting dark red paste-like suspension (internal temperature=122° C.). Subsequently, 22.90 g (0.150 mol) of VBC, diluted with 20 ml of DMF, are then added dropwise over 30 minutes. After the addition is complete, the dark red suspension, which is now markedly more liquid, is stirred at 120–125° C. After a reaction time of 2⅔ h (from the addition of the VBC), the mixture is cooled to room temperature and filtered through a filter covered with polysilicic acid (HYFLO®Supercel, of Ciba Specialty Chemicals) as filter aid and is then concentrated under vacuum at 60° C., the orange product precipitating in small lumps. The crude product, which also contains a small amount of dark brown oil, is mixed with 400 ml of ethanol under reflux conditions, upon which a very fine suspension forms. After the suspension is cooled with a mixture of ice and water, it is filtered and the pale orange filter residue is then washed with cold ethanol and dried under vacuum at 50–60° C. The crude product is recrystallised twice from DMF. DPP I yield (with A=B=Ph, $R_1$=$R_2$=—$CH_2$—(para—Ph)—CH=$CH_2$): 23.98 g (92.1%), melting point: 120° C. (polymerised spontaneously during melting).

Example 2

(a) Preparation of the starting compound 29.8 g (0.12 mol) of the pyrrolinone

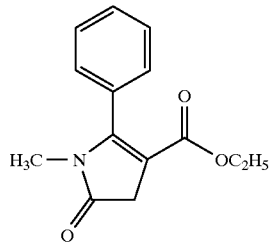

prepared in analogy to the method described in Example 4 of U.S. Pat. No. 4,778,899, and 18.16 g (0.132 mol) of p-chlorobenzonitrile are placed in a reactor flushed with nitrogen and then 180 ml of 2-methyl-1-pentanol are added. This mixture is heated to 110–115° C. until, after about 30 minutes, a clear pale brown solution is obtained. 12.96 g (0.24 mol) of 30% sodium methylate in saturated sodium hydroxide solution are then added over 2 hours at a stirring speed of 510 to 520 revolutions/minute while simultaneously distilling off the forming methanol/ethanol mixture. The mixture is stirred for about 1 hour at the same temperature and is then cooled to room temperature. After adding 500 ml of methanol, the mixture is acidified with 57.7 g (0.96 mol) of acetic acid. After vigorously stirring the resulting thick paste, the product precipitates after about 3 minutes in an intensely orange-red shade. The product is diluted with another 100 ml of methanol and 150 ml water and the orange-red suspension is subjected to filtration. The filter cake is washed with 150 ml of methanol in 3 portions and dried overnight in a vacuum drying oven at 60–70° C., giving 25.53 g (63.2% of theory) of the diketopyrrolopyrrole of formula

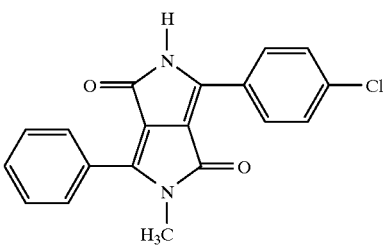

(b) 16.85 g (0.05 mol) of the DDP derivative prepared according to (a) and 180 ml of DMF are heated under nitrogen to 120–125° C. To the resultant dark red suspension are added 6.91 g (0.05 mol) of potassium carbonate, dried at 250° C., and then 0.04 g (0.5% in VBC) of hydroquinone. 11.45 g (0.075 mol) of VBC, diluted with 10 ml of DMF, are added dropwise over 30 minutes at an internal temperature of 124° C. After the addition of VBC is complete, the highly liquid dark red suspension is stirred at 120–125° C. After 2h 25' (from the addition of the VBC) DPP starting material can no longer be detected. After another 20 minutes the dark red suspension is cooled to room temperature and filtered through a filter covered with polysilicic acid (see Example 1) and concentrated completely at 60° C. under vacuum. The dark red oil obtained is dissolved in 400 ml of ethanol. The suspension formed during cooling is cooled with a mixture of ice and water, filtered and then washed with cold ethanol and dried under vacuum at 40–50° C. The new product is dark red and is recrystallised in ethanol. DPP I yield (with A=Ph, B=p—Cl—Ph, $R_2$=Me, $R_1$=—$CH_2$—(p—Ph)—CH=$CH_2$): 13.07 g (57.7%), melting point: 130° C. (polymerised spontaneously during melting),

| elemental analysis: | C | H | N | Cl |
|---|---|---|---|---|
| | 74.25 | 4.67 | 6.18 | 7.83 calcd. |
| | 73.98 | 4.71 | 6.14 | 7.76 found |

Example 3

Preparation of a polymer by photochemical polymerisation 3 g of a photocurable formulation consisting of 88.8 parts of a commercially available acryl monomer mixture (c. 80%, dissolved in 1,6-hexanedioldiacrylate, LAROMER®EA 81, BASF), 5 parts of the DPP monomer prepared in Example 1, 1.55 parts of a photoinitiator I (a bis-acylphosphine oxide type), 4.65 parts of a second photoinitiator II (IRGACURE®184, a α-hydroxyalkylphenone, of Ciba Specialty Chemicals) are initially heated to 188° C. for 4 to 5 minutes. The mixture is then stirred and heated for another 5 to 6 minutes to 188° C. and stirred again until there are hardly any solids visible anymore. Volatile components are then removed under vacuum and the mixture is heated for another 2 to 3 minutes to 188° C.

Using a 50 μm coating knife, films are drawn onto pretreated aluminium plates which are then exposed using a Hönle UV lamp (intensity 51–53%, distance 19 to 20 cm). The golden yellow films are cured after an exposure time of 25 seconds.

Example 4

The photostability is tested with an ATLAS Weatherometer Type CI 35. The characteristic data for the tests:
operating capacity of the apparatus at 420 nm: 0.92 W/m2
operating capacity of the xenon burner at 0.92 W/m2 : 3000 W irradiation cycle in h: 90.4
irradiation cycle in kJ/m2 at 420 nm: 299.4 kJ/m2
type of irradiation: continuously
black standard temperature: 62° C.
test room temperature: 43±3° C.
rel. atmospheric humidity: 50 ±5%

The photostability is assessed by measuring the optical density after each exposure in the Weather—O—meter and is expressed in % of the original optical density (O.D.) after x h exposure in the apparatus.

This formulation results after 1000 h in an O.D. of about 80% and thus has excellent photo-stability.

Example 5

Preparation of a DPP derivative of formula V (a) 34.60 g (0.12 mol) of the diketopyrrolopyrrole of formula III, with A=B=phenyl and $R_{14}$=hydrogen (obtainable according to Example 1 of U.S. Pat. No. 4,579,949), 49.76 g.(0.36 mol) of potassium carbonate (dried at 350° C.) and 600 ml of freshly distilled dimethylformamide are heated under nitrogen to 130–135° C. With vigorous stirring, 51.80 g (0.36 mol) of 95% 6-chloro-1-hexanol are added dropwise over about 10 minutes at this temperature. After the addition is complete, the dark red suspension is stirred for another 2 hours at 130–135° C. and then at room temperature overnight. The resulting dark red solution containing suspended material (KCl, $K_2CO_3$) is filtered and the filter cake is washed three times with 25 ml DMF. Stirring well, the filtrate is added to 2 l of distilled water, upon which an orange product precipitates. The mixture is heated to boiling and filtered at 94° C. The tacky red mass remaining in the filter is dissolved hot in 800 ml of ethanol, concentrated to about 300 ml and left to stand overnight. An orange product precipitates which, after cooling in ice water, is collected by filtration and recrystallised in ethanol, giving 15.1 g (26.5% of theory) of an orange crystalline product of formula V, wherein A=B=phenyl and $R_{15}$=$R_{16}$=—($CH_2$)$_6$—OH (t=v=0, U=$C_6$alkylene, Q=—OH).

(b) 19.55 g (0.04 mol) of the product prepared in (a), 0.04 g (0.2 mmol) of phenothiazine and 380 ml of dichloroethane are refluxed under nitrogen. With refluxing (80° C.) and stirring, 14.48 g (0.16 mol) of acrylic acid chloride are added dropwise to the turbid orange solution over about 30 minutes. After the addition is complete, the mixture is flushed with 20 ml of dichloroethane. With stirring, the yellowish orange solution is refluxed for 7 hours, cooled to room temperature and left to stand overnight. The orange-red, very slightly turbid solution is washed in a separating funnel 5 times with 100 ml of 5% sodium hydroxide solution and 2 times with deionised water, dried over $MgSO_4$—$H_2O$ and filtered. The orange-red clear filtrate is completely concentrated by evaporation in a rotary evaporator. The red oil remaining solidifies overnight to form a solid mass which is recrystallised from ethanol, giving 23.1 g (96.7% of theory) of a crystalline product of formula

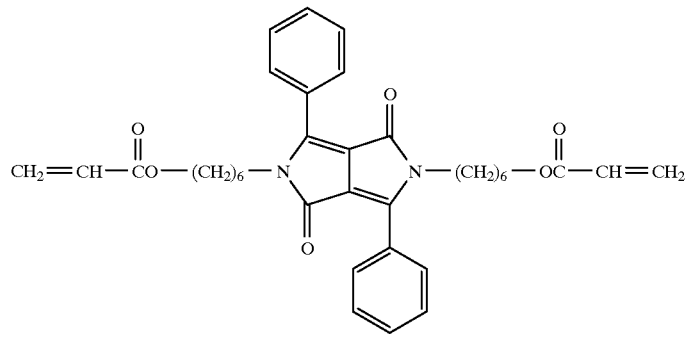

having a melting point of 79.7–80.1° C.

Example 6

5 g each of the formulations are prepared. The components are placed in a test tube and stirred with a glass rod, and the mixture is then heated at 140° C. (mixture) until a clear orange-red viscous solution is formed by stirring. The films are drawn onto pretreated aluminium plates using a 50 μm coating knife. Exposure is carried out using a Hönle UV lamp. Conditions: capacity c. 92.5 mW/cm², intensity 50–52%, distance 19–20 cm. The following Table gives the amounts of the starting compounds and some of the reaction conditions.

TABLE

| formulation | 1 | 2 | 3 | 4 | 5 | 6 | 7 | 8 | 9 | 10 | 11 |
|---|---|---|---|---|---|---|---|---|---|---|---|
| Ex. 5 | 10% | 9% | 8% | 7% | 6% | 5% | 4% | 3% | 2% | — | — |
| Ex. 1 | — | 1% | 2% | 3% | 4% | 5% | 6% | 7% | 8% | 10% | 4% |
| monomer I | 83.8% | 83.6% | 83.8% | 83.8% | 83.8% | 83.8% | 83.8% | 83.8% | 83.8% | 83.8% | 89.8% |
| PI I | 2.5% | 2.5% | 2.5% | 2.5% | 2.5% | 2.5% | 2.5% | 2.5% | 2.5% | 2.5% | 2.5% |
| PI II | 3.7% | 3.7% | 3.7% | 3.7% | 3.7% | 3.7% | 3.7% | 3.7% | 3.7% | 3.7% | 3.7% |
| processing temp. | 80° C. | 140° C. | 140° C. | 140° C. | 140° C. | 140° C. | 140° C. | 140° C. | 140° C. | ca. 190° C. | 150° C. |
| pot life | >2 h | | 60 min | | 60 min | | 50 min | | 50 min | ≦15' | |
| photocuring time | 7' | | 5.5' | | 5' | | 4.5' | | 4' | | 0.5' |

TABLE-continued

| formulation | 1 | 2 | 3 | 4 | 5 | 6 | 7 | 8 | 9 | 10 | 11 |
|---|---|---|---|---|---|---|---|---|---|---|---|
| colour difference $\Delta E^*_{ab}$ | | | | | | | | | 2.6 | | 1.8 |

The monomer I used is LAROMER®EA 81 (see Example 3);

PI I signifies photoinitiator I; the photoinitiator I of Example 3 is used; PI II signifies photoinitiator II; the photoinitiator II of Example 3 is used.

The colour difference $\Delta E^*_{ab}$ is determined in a Weather—O—meter, first determining the colour values $L^*_1$, $a^*_1$ and $b^*_1$ of the CIE colour space (Commission Internationale de l'Eclairage) before exposure and, after 1000 hours of exposure, determining the changed colour values $L^*_2$, $a^*_2$ and $b^*_2$. The colour difference $\Delta E^*_{ab}$ is obtained from the ratio $$\Delta E^*_{ab} = \sqrt{(\Delta L^*)^2 + (\Delta a^*)^2 + (\Delta b^*)^2},$$

Wherein $\Delta L^* = L^*_2 - L^*_1$; $\Delta a^* = a^*_2 - a^*_1$; $\Delta b^* = b^*_2 - b^*_1$ The pot life is the time during which the respective mixture can be processed before (premature) polymerisation takes place.

As may be gathered, the mixtures have excellent processing characteristics and at the same time a very short photocuring time. Moreover, the colour difference $\Delta E^*_{ab}$ is a measure of the photostability. In accordance therewith, the photostability is the better, the lower the colour difference $\Delta E^*_{ab}$. The colour differences found above (formulations 9 and 11) are very good values.

The following Examples are all carried out under a nitrogen protective gas atmosphere:

Example 7

171.1 g of a 40% peracetic acid solution are added dropwise over 40 min to a mixture, heated to 40° C., consisting of 91.6 g of VBC, 16.4 g of sodium acetate and 400 ml of ethyl acetate. Using a water bath, the reaction temperature is controlled such that it does not rise above 45° C. The course of the reaction is controlled by gas chromatography. The reaction is stopped after 3 h (product content 70–75%) and the reaction solution is worked up immediately by shaking it out with a 10% sodium hydrogen carbonate solution (c. 1 liter in total) until no great formation of foam can be detected any longer. The organic phases are dried over magnesium sulfate and filtered, and the filtrate is then concentrated in a rotary evaporator. The crude product is purified by high-vacuum distillation. Yield: 50% (after distillation), purity (GC): 99%.

Example 8

41.5 g of potassium carbonate are added to a suspension, heated to 80° C., consisting of 28.8 g of a commercially available DPP pigment (starting from formula 1, A=B=phenyl and $R_1=R_2=H$) and 750 ml of DMF, and this mixture is stirred for 5 minutes. Subsequently, 50.6 g of the epoxy compound of Example 7 are added dropwise over 5 minutes. The reaction mixture is stirred for 4 h at 80° C. and is then filtered at this temperature through a filter covered with a filter aid (see Example 1). The filtrate is then concentrated under high vacuum. 900 ml of ethyl acetate are added, with stirring, to the paste-like residue and the suspension so obtained is left to stand overnight. It is then filtered and dried in a vacuum oven at 60° C.

Yield: 39.0 g (69% of theory); m.p.: 188° C.

Example 9

A mixture consisting of 19.3 g of the epoxy-substituted DPP derivative of Example 8, 420 g of diethylene glycol monomethyl ether and 0.3 ml of a 50% aqueous $Sn(BF_4)_2$ solution is heated for 1 hour to 110° C. The solution obtained is then concentrated in a reduced pressure atmosphere and the concentrated solution is dissolved in 100 ml of ethanol and then precipitated in ice water. After filtration, the filter residue is recrystallised in ethanol. Yield: 19.2 g (70%). M.p.: 85–90° C.

Example 10

15.8 g of the product obtained in Example 9, 10 mg of thiodiphenylamine and 100 ml of dichloroethane are heated to a temperature in the range from 80–85° C. 7.24 g of acrylic acid chloride are then added dropwise over 1 hour. After stirring for 4.5 h at 80–85° C., the reaction is stopped by cooling to room temperature. The mixture so obtained is then shaken out in a separating funnel with 3×100 ml each of 1N NaOH and 3×100 ml each of deionised water. The combined organic phases are dried over magnesium sulfate and filtered, and the filtrate is completely concentrated in a rotary evaporator. The oily residue is dissolved in 100 ml of ethanol and the ethanolic solution is cooled in ice water for 2 hours and then filtered. The filter residue is washed with cold ethanol and dried in a reduced pressure atmosphere at room temperature. Yield: 16.5 g (92%); m.p.: 75–80° C.

What is claimed is:

1. A diketopyrrolopyrrole of formula I

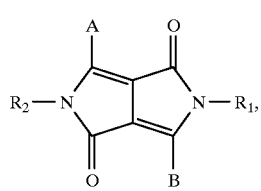

(I)

wherein $R_1$ is a group of formula II

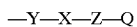

—Y—X—Z—Q (II), wherein

Y is —$CR_3R_4$—, —$SO_2$—, —CO—, —Si(Hal)$_2$—, —POHal—, wherein $R_3$ and $R_4$ are each independently of the other hydrogen or $C_1$–$C_4$alkyl, and Hal is halogen, X is an unsubstituted or substituted carbocyclic or heterocyclic arylene group, Z is a single bond, uninterrupted linear or branched $C_1$–$C_{30}$alkylene, or linear or branched $C_2$–$C_{30}$alkylene which is interrupted once or more than once by a hetero atom, —CH═CH—, —C≡C—, —N═CH—, —CH═N— or —NH—, or is $C_5$–$C_{12}$cycloalkylene, Q is —OH, —SH, —NH$_2$, glycidyl, 1,2-epoxyethyl,

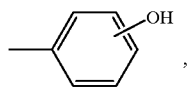

—CHO, —NCO, —CH═CH$_2$, —C(CH$_3$)═CH$_2$, —OCO—CH═CH$_2$, —OCO—C(Me)═CH$_2$, —CH$_2$—CH═CH$_2$, —CH$_2$—OH, —CO—CH═CH$_2$, —CO—C(CH$_3$)═CH$_2$, $C_5$–$C_7$cycloalkenyl,

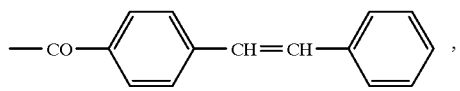

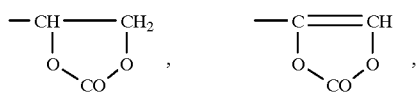

—CONHR$_6$, —COOR$_6$, —COR$_6$, wherein R$_6$ is hydrogen or $C_1$–$C_6$alkyl,

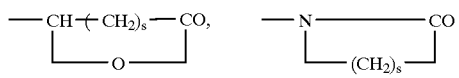

wherein s is an integer from 1 to 6, and

R$_2$ is $C_1$–$C_6$alkyl,

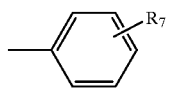

or R$_1$, and

R$_7$ is hydrogen or $C_1$–$C_6$alkyl, and

A and B are each independently of the other a group of formula

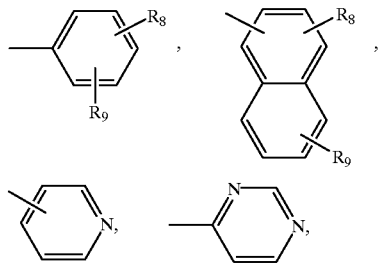

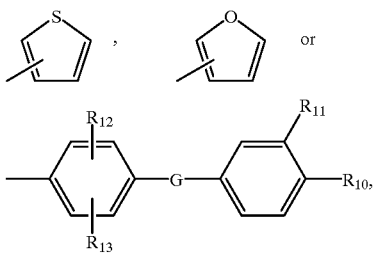

wherein

R$_8$ and R$_9$ are each independently of the other hydrogen, halogen, $C_1$–$C_{18}$alkyl, $C_1$–$C_{18}$alkoxy, $C_1$–$C_{18}$alkylmercapto, $C_1$–$C_{18}$alkylamino, $C_1$–$C_{18}$alkoxycarbonyl, $C_1$–$C_{18}$alkylaminocarbonyl, —CN, —NO$_2$, trifluoromethyl, $C_5$–$C_6$cycloalkyl, —CH═N—($C_1$–$C_{18}$alkyl);

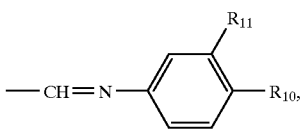

imidazolyl, pyrrazolyl, triazolyl, piperazinyl, pyrrolyl, oxazolyl, benzoxazolyl, benzothiazolyl, benzimidazolyl, morpholinyl, piperidinyl or pyrrolidinyl, G is —CH$_2$—, —CH(CH$_3$)—, —C(CH$_3$)$_2$—, —CH═N—, —N═N—, —O—, —S—, —SO—, —SO$_2$—, —CONH— or —NR$_7$—, R$_{10}$ and R$_{11}$ are each independently of the other hydrogen, halogen, $C_1$–$C_6$alkyl, $C_1$–$C_{18}$alkoxy or —CN, R$_{12}$ and R$_{13}$ are each independently of the other hydrogen, halogen or $C_1$–$C_6$alkyl.

2. A coloured composition comprising a high molecular weight organic material and a diketopyrrolopyrrole of formula (I) according to claim 1.

3. A diketopyrrolopyrrole of formula

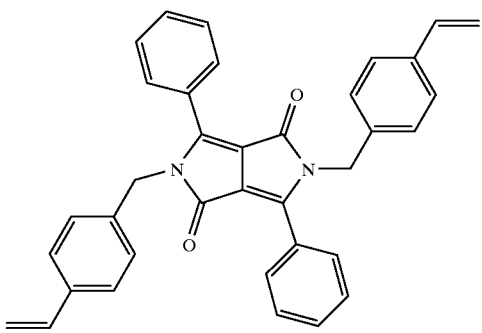

* * * * *